(12) United States Patent
Sato

(10) Patent No.: US 11,759,127 B2
(45) Date of Patent: Sep. 19, 2023

(54) AUTHENTICATION DEVICE, AUTHENTICATION SYSTEM, AUTHENTICATION METHOD, AND NON-TRANSITORY STORAGE MEDIUM STORING PROGRAM

(71) Applicants: OMRON HEALTHCARE Co., Ltd., Kyoto (JP); OMRON Corporation, Kyoto (JP)

(72) Inventor: Hironori Sato, Kyoto (JP)

(73) Assignees: OMRON CORPORATION, Kyoto (JP); OMRON HEALTHCARE CO., LTD., Kyoto (JP)

( * ) Notice: Subject to any disclaimer, the term of this patent is extended or adjusted under 35 U.S.C. 154(b) by 283 days.

(21) Appl. No.: 16/871,134

(22) Filed: May 11, 2020

(65) Prior Publication Data

US 2020/0272721 A1 Aug. 27, 2020

Related U.S. Application Data

(63) Continuation of application No. PCT/JP2018/041712, filed on Nov. 9, 2018.

(30) Foreign Application Priority Data

Nov. 16, 2017 (JP) ................................. 2017-220685

(51) Int. Cl.
*A61B 5/117* (2016.01)
*H04W 4/80* (2018.01)
(Continued)

(52) U.S. Cl.
CPC .............. *A61B 5/117* (2013.01); *G06F 21/32* (2013.01); *G06V 40/40* (2022.01); *H04B 5/0031* (2013.01); *H04B 11/00* (2013.01); *H04W 4/80* (2018.02)

(58) Field of Classification Search
CPC . G06F 21/32; G06F 2221/2139; G06V 10/60; G06V 40/40; H04B 5/0031;
(Continued)

(56) References Cited

U.S. PATENT DOCUMENTS 10,701,067 B1* 6/2020 Ziraknejad ............ H04W 12/63
2012/0036261 A1 2/2012 Salazar et al.
(Continued)

FOREIGN PATENT DOCUMENTS

JP 2006-331048 A 12/2006
JP 2013-535924 A 9/2013
(Continued)

OTHER PUBLICATIONS

International Preliminary Report on Patentability and Written Opinion of the International Searching Authority dated May 28, 2020 in International (PCT) Application No. PCT/JP2018/041712.
(Continued)

*Primary Examiner* — Eugene Yun
(74) *Attorney, Agent, or Firm* — Wenderoth, Lind & Ponack, L.L.P.

(57) ABSTRACT

An authentication device according to an aspect of the present invention includes an acquisition unit configured to acquire measurement data including a measured value and measurement time information associated with the measured value from a biological information measuring device configured to measure a value related to biological information, a provision unit configured to provide a function to be used by one specific user, a sensor unit including at least one sensor, an estimation unit configured to estimate, on the basis of information acquired by the sensor unit, a state of the one specific user during a time range specified by the measurement time information, and an identification unit configured to identify whether the measured value pertains to the one specific user on the basis of whether the function is in an enabled state during the time range and an estimation result of the state.

8 Claims, 6 Drawing Sheets

(51) Int. Cl.
*G06F 21/32* (2013.01)
*H04B 5/00* (2006.01)
*H04B 11/00* (2006.01)
*G06V 40/40* (2022.01)

(58) Field of Classification Search
CPC .......... H04B 11/00; H04B 4/80; A61B 5/022; A61B 5/1112; A61B 5/1118; A61B 5/117
See application file for complete search history.

(56) References Cited

U.S. PATENT DOCUMENTS

| | | | |
|---|---|---|---|
| 2016/0007158 A1* | 1/2016 | Venkatraman | H04W 4/023 455/456.2 |
| 2016/0253489 A1 | 9/2016 | Yamashita et al. | |
| 2017/0293763 A1* | 10/2017 | Shear | G06F 21/32 |
| 2017/0295173 A1* | 10/2017 | Walsh | H04W 12/08 |

FOREIGN PATENT DOCUMENTS

| | | | |
|---|---|---|---|
| JP | 2015-108942 A | 6/2015 | |
| JP | 2016-77359 A | 5/2016 | |

OTHER PUBLICATIONS

International Search Report of the International Searching Authority for PCT/JP2018/041712 dated Feb. 12, 2019.
English translation of International Search Report of the International Searching Authority for PCT/JP2018/041712 dated Feb. 12, 2019.

* cited by examiner

| MEASUREMENT CONTENT | STATE BEFORE MEASUREMENT | STATE DURING MEASUREMENT | STATE AFTER MEASUREMENT |
|---|---|---|---|
| BLOOD PRESSURE MONITOR WEIGHT AND BODY COMPOSITION METER THERMOMETER ELECTROCARDIOGRAPH | DYNAMIC | STATIC | DYNAMIC |
| ACTIVITY METER PEDOMETER | STATIC | DYNAMIC | STATIC |

FIG. 6

AUTHENTICATION DEVICE, AUTHENTICATION SYSTEM, AUTHENTICATION METHOD, AND NON-TRANSITORY STORAGE MEDIUM STORING PROGRAM

CROSS-REFERENCE TO RELATED APPLICATIONS

This is a continuation of International Application 2017-220685, with an international filing date of Nov. 16, 2017, and PCT/JP2018/041712 with an international filing date of Nov. 9, 2018 and filed by applicant, the disclosure of which is hereby incorporated by reference in its entirety.

TECHNICAL FIELD

The present invention relates to technology for authenticating a measurement result acquired using a biological information measuring device.

BACKGROUND ART

There have been proposed systems that allow a user to receive a service, such as a cash back, when the user improves his or her lifestyle. Such a system determines whether the user has improved his or her lifestyle by measuring a value related to biological information of the user using a biological information measuring device, and analyzing the acquired measurement result. Therefore, reliability in that the measurement result pertains to the user himself or herself needs to be ensured.

JP 2015-108942 A discloses technology for determining whether a measurement result pertains to a user by confirming the presence or absence of logical inconsistencies between a measurement result acquired by a biological information acquisition device and another measurement result acquired by another type of biological information acquisition device.

SUMMARY OF INVENTION

In a system such as that described above, spoofing in which a person different from the user (intended person) to be measured carries out measurement using the biological information measuring device needs to be detected.

The present invention has been made with reference to the above circumstances, and an object of the present invention is to provide an authentication device, an authentication system, an authentication method, and a non-transitory storage medium storing a program capable of detecting spoofing in which a person different from the intended person carries out measurement using a biological information measuring device.

To solve the problems described above, the present invention adopts the following configuration.

An authentication device according to an aspect of the present invention includes an acquisition unit configured to acquire measurement data including a measured value and measurement time information associated with the measured value from a biological information measuring device configured to measure a value related to biological information, a provision unit configured to provide a function to be used by one specific user, a sensor unit including at least one sensor, an estimation unit configured to estimate, on the basis of information acquired by the sensor unit, a state of the one specific user during a time range specified by the measurement time information, and an identification unit configured to identify that the measured value pertains to the one specific user in a case where the function is in an enabled state during the time range and an estimation result of the state shows that the state is appropriate for measurement.

In the configuration described above, measurement data including a measured value and measurement time information are acquired from the biological information measuring device, a personalized function to be used by one specific user (for example, a user who is the owner of the authentication device) is provided, the state of the user during measurement is estimated on the basis of the information acquired by the sensor unit, and whether the measured value pertains to the user is identified on the basis of whether the personalized function was in an enabled state during measurement and the estimation result of the state. When the personalized function is in an enabled state, it is ensured that the authentication device is held (carried or worn) by the specific user. Thus, in a case where the personalized function is in an enabled state during measurement, the estimation result of the state during measurement can be regarded as a result that pertains to the specific user. Further, in a case where the specific user himself or herself carries out measurement using the biological information measuring device, the specific user should be in a state appropriate for measurement. Accordingly, the measured value can be authenticated on the basis of whether the personalized function is in an enabled state during measurement and whether the estimation result shows that the state during measurement is appropriate for measurement. As a result, it is possible to detect spoofing in which a person different from the specific user carries out measurement using the biological information measuring device.

In the authentication device according to the aspect described above, the state of the one specific user may be a behavioral pattern indicating a behavior of the one specific user, for example, and the identification unit may be configured to identify that the measured value pertains to the one specific user in a case where the function is in an enabled state during the time range and a behavioral pattern estimated by the estimation unit matches a reference behavioral pattern predetermined in accordance with a type of the biological information, and to identify that the measured value does not pertain to the one specific user in a case where the function is not in an enabled state during the time range or the behavioral pattern estimated by the estimation unit does not match the reference behavioral pattern predetermined in accordance with the type of the biological information.

In the configuration described above, the behavior of the user during measurement is estimated, and the measurement data is authenticated on the basis of a comparison between the behavioral pattern acquired by the estimation and the reference behavioral pattern predetermined in accordance with the type of biological information. The behavior of the user can be estimated using a sensor provided to a general portable or wearable device, such as an acceleration sensor, a gyro sensor, or a position sensor, and thus a sensor need not be newly provided for authentication. As a result, the authentication device can be achieved at low cost.

In the authentication device according to the aspect described above, the time range includes a time range before measurement, a time range during measurement, and a time range after measurement, and the behavioral pattern includes information indicating whether the one specific user is in a dynamic state or a static state during each of the time range before measurement, the time range during measurement, and the time range after measurement.

In the configuration described above, the measurement data is authenticated on the basis of the behavior of the user before measurement, during measurement, and after measurement. By taking into account the behavior not only during measurement but also before and after measurement, it is possible to more accurately authenticate the measurement data.

In the authentication device according to the aspect described above, the state of the one specific user may be a state indicating whether the one specific user is in a predetermined environment, for example. For example, the sensor unit includes an optical sensor configured to detect a surrounding brightness, the estimation unit is configured to estimate whether the one specific user is in a bright location or a dark location during the time range on the basis of the surrounding brightness that is detected, and the identification unit is configured to identify that the measured value pertains to the one specific user in a case where the one specific user is estimated to be in the bright location by the estimation unit, and to identify that the measured value does not pertain to the one specific user in a case where the one specific user is estimated to be in the dark location by the estimation unit.

In the configuration described above, the environment in which the user exists during measurement is estimated, and the measurement data is authenticated using the estimation results. The environment can be estimated using a sensor provided to a general portable or wearable device, such as an optical sensor, and thus a sensor need not be newly provided for authentication. As a result, the authentication device can be achieved at low cost.

In the authentication device according to the aspect described above, the acquisition unit may be configured to acquire the measurement data by near-field wireless communication with the biological information measuring device.

In the configuration described above, the authentication device is capable of receiving measurement data from the biological information measuring device when it is near the biological information measuring device. In a case where another user carries out measurement using the biological information measuring device and the authentication device is positioned away from the biological information measuring device, the authentication device does not acquire the measurement data that pertains to that user. Accordingly, mistaken acquisition of measurement data that pertains to another user can be prevented.

In the authentication device according to the aspect described above, the near-field wireless communication may be, for example, ultrasonic communication. Ultrasonic communication has a short communication distance, making it possible to more effectively prevent mistaken acquisition of measurement data that pertains to another user.

According to the present invention, it is possible to provide an authentication device, an authentication system, an authentication method, and a non-transitory storage medium storing a program capable of preventing spoofing in which a person different from the intended person measures biological information.

BRIEF DESCRIPTION OF DRAWINGS

FIG. 6 is a diagram illustrating a reference behavioral pattern according to an embodiment of the present invention.

DESCRIPTION OF EMBODIMENTS

Figure 1:
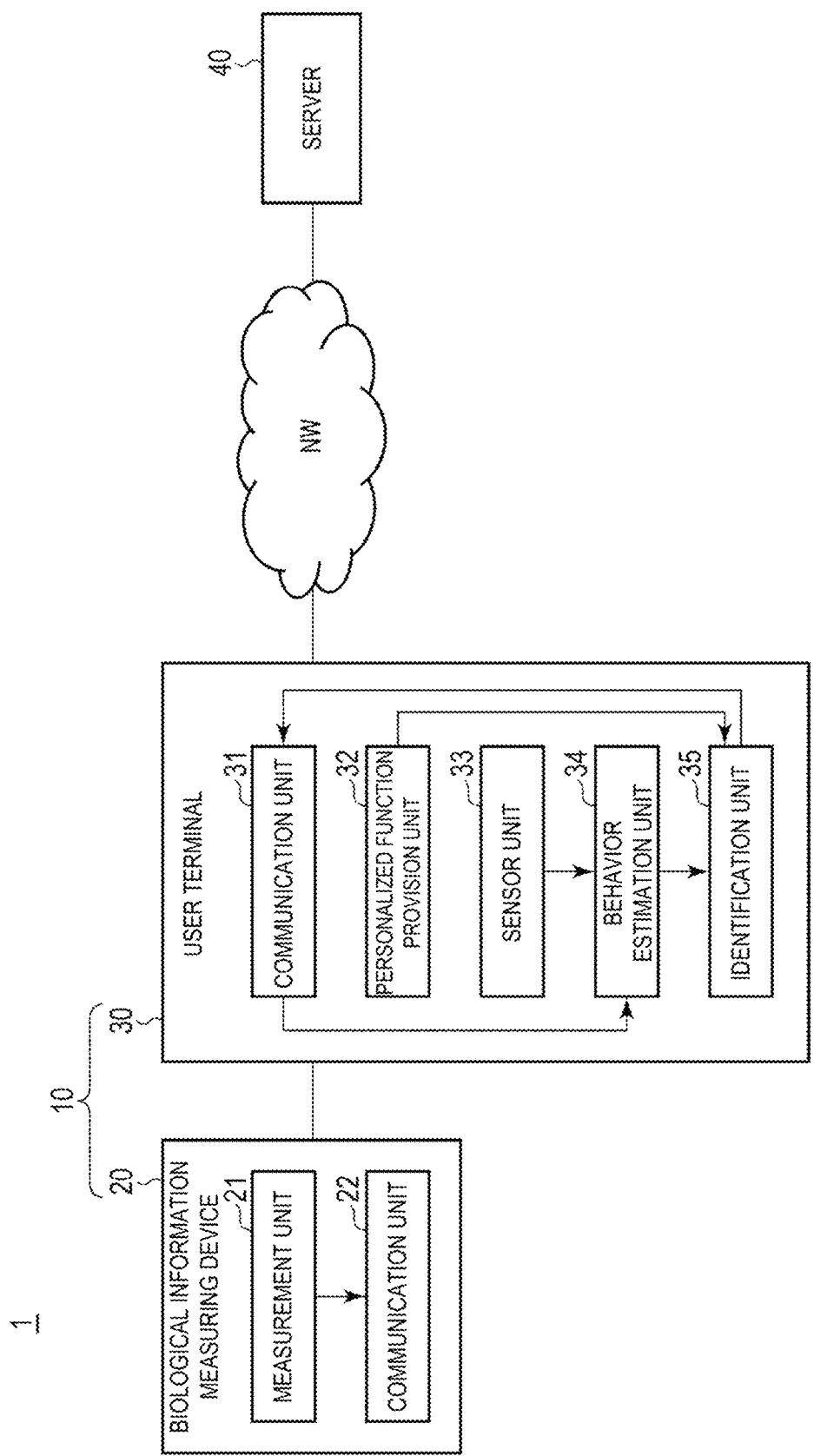
FIG. 1 is a block diagram illustrating an example of an authentication system according to an embodiment of the present invention.

Embodiments of the present invention will be described below with reference to the drawings.
Application Example With reference to FIG. 1, an example of a case to which the present invention is applied will be described. FIG. 1 illustrates an information processing system 1 including an authentication system 10 according to an embodiment of the present invention. In the information processing system 1, the authentication system 10 communicates with a server 40 through a network NW, such as the Internet. The authentication system 10 includes a biological information measuring device 20 and a user terminal 30. The user terminal 30 corresponds to the "authentication device" of the present invention.

As an example, the information processing system 1 is applied to a system for computing insurance premiums. For example, when an insured improves his or her lifestyle, the insurance company reduces the insurance premium when the insurance is renewed. In this case, the insured uses the biological information measuring device 20 provided or designated by the insurance company. Measurement data including a measurement result acquired by the biological information measuring device 20 is transmitted to the server 40 via the user terminal 30 owned by the insured. The insurance company acquires the measurement data from the server 40 and determines whether the insured has improved his or her lifestyle on the basis of the acquired measurement data.

In this example, it is necessary to ensure that the measurement result acquired by the biological information measuring device 20 pertains to the insured. In the present embodiment, the user terminal 30 identifies whether the measurement result pertains to the insured. Hereinafter, a user who is to carry out measurement, such as the insured, is referred to as an intended user.

The authentication system 10 will now be described.

The biological information measuring device 20 includes a measurement unit 21 and a communication unit 22.

The measurement unit 21 measures a value related to biological information, and generates measurement data including a measured value and measurement time information associated with the measured value. The biological information is information related to the human body and/or behavior. Examples of the biological information include blood pressure, electrocardiogram, heart rate, pulse, body temperature, weight, body composition, step count, and amount of activity. The body composition indicates a percentage or an amount of tissue that constitutes the body. The body composition is, for example, body fat percentage, muscle percentage, lean fat mass, body fat mass, muscle mass, bone mass, and water content. The amount of activity is information indicating physical activity, including walking, housework, and desk work. The amount of activity is, for example, calories burned (amount of metabolizable energy). Thus, the biological information measuring device 20 is, for example, a blood pressure monitor, an electrocardiograph, a heart rate monitor, a pulse rate meter, a thermometer, a scale, a body composition meter, a pedometer, an activity meter, or the like. The measurement time information is information indicating a time at which a measurement was carried out.

The communication unit 22 exchanges data with the user terminal 30. For example, the communication unit 22 transmits measurement data generated by the measurement unit 21 to the user terminal 30. The communication unit 22 corresponds to the "transmission unit" of the present invention. The communication unit 22 may receive time information from the user terminal 30. In this case, time synchronization is performed between the biological information measuring device 20 and the user terminal 30. The time synchronization between the biological information measuring device 20 and the user terminal 30 makes it possible to accurately perform authentication processing described later. The time synchronization may be performed by the biological information measuring device 20 and the user terminal 30 receiving a reference time from another device (for example, the server 40).

The user terminal 30 is a portable or wearable device. The user terminal 30 includes a communication unit 31, a personalized function provision unit 32, a sensor unit 33, a behavior estimation unit 34, and an identification unit 35. Below, the personalized function provision unit is simply referred to as a provision unit.

The communication unit 31 exchanges data with the biological information measuring device 20. For example, the communication unit 31 receives measurement data from the biological information measuring device 20. The communication unit 31 corresponds to the "acquisition unit" of the present invention.

The provision unit 32 provides a personalized function that is a function to be used by one specific user. In the present specification, a personalized function is a function that, when a user (another person) different from the one specific user uses the function, may cause the specific user to lose confidence in society. Examples of personalized functions include a telephone function, an email function, a credit card function, an e-money function, and a personal identification (ID card) functions. Here, the personalized function is a function personalized for the intended user. The personalized function may be activated and changed to an enabled state (that is, made active) along with activation of the user terminal 30 or may be activated and changed to an enabled state in response to an instruction from the user. Further, the personalized function may also request input of a password during activation, and change to an enabled state when the correct password is entered. Use of an authentication technique such as a password more reliably ensures that the intended user is holding the user terminal 30 when the personalized function is in an enabled state.

The sensor unit 33 includes one or a plurality of sensors that acquire information pertaining to the state of the user terminal 30. In the present embodiment, the sensor unit 33 is configured to detect movement of the intended user and includes, for example, at least one of an acceleration sensor, a gyro sensor, and a position sensor.

The behavior estimation unit 34 estimates a behavioral pattern of the user during a time range (hereinafter, also referred to as a measurement time range) specified by the measurement time information included in the measurement data, on the basis of the information acquired by the sensor unit 33. For example, the behavioral pattern includes information indicating whether the intended user was in a static state or a dynamic state before measurement, during measurement, and after measurement. For example, the dynamic state is a state in which there is movement, such as walking, and the static state is a state in which there is no movement. Note that movement need not involve a change in location. For example, the behavior estimation unit 34 determines that the intended user is in a dynamic state when movement not suitable for measurement, such as a jumping in place, is detected. Further, specific movements, including movements for operating a device, such as the biological information measuring device 20, are also permitted. The behavior estimation unit 34 corresponds to the "estimation unit" of the present invention. The behavioral pattern is an example of a state of the intended user.

The identification unit 35 identifies whether the measured value included in the measurement data pertains to the intended user on the basis of whether the personalized function was in an enabled state during the measurement time range and an estimation result of the state output from the behavior estimation unit 34. Specifically, the identification unit 35 identifies that the measured value pertains to the intended user in a case where the personalized function is in an enabled state during the measurement time range and the estimation result of the state shows that the state is appropriate for measurement, and identifies that the measured value does not pertain to the intended user in a case where the personalized function is not in an enabled state during the measurement time range or the estimation result of the state shows that the state is not appropriate for measurement. In the present embodiment, to identify whether the measured value included in the measurement data pertains to the intended user, the identification unit 35 determines whether the behavioral pattern estimated by the behavior estimation unit 34 matches a reference behavioral pattern predetermined in accordance with the type of biological information. The identification unit 35 identifies that the measured value pertains to the intended user in a case where the identification unit 35 determines that the estimated behavioral pattern matches the reference behavioral pattern, and identifies that the measured value does not pertain to the intended user in a case where the identification unit 35 determines that the estimated behavioral pattern does not match the reference behavioral pattern.

For example, during blood pressure measurement, the intended user should be still. Presume, however, that in contrast, the user terminal 30 detects that the intended user is moving during blood pressure measurement. In this case, another user different from the intended user is considered to have carried out a measurement using the biological information measuring device 20, and thus the measured value acquired by the biological information measuring device 20 is not identified as pertaining to the intended user. Even given that the measured value pertains to the intended user, the measured value is acquired in a state in which the intended user moved, and thus the reliability of the measured value is low. Therefore, this measured value should not be subjected to analysis, and is identified as not pertaining to the intended user.

In the user terminal 30 having the above-described configuration, the personalized function is a function personalized for the intended user, and when the personalized function is in an enabled state, it is ensured that the specific user holds (carries or wears) the user terminal 30. Thus, in a case where the personalized function is in an enabled state during measurement, the estimation result of the state during measurement can be regarded as a result pertaining to the intended user. Further, in a case where the intended user himself or herself carries out measurement using the biological information measuring device 20, the intended user should be in a state appropriate for measurement. Accordingly, the measured value included in the measurement data can be authenticated on the basis of whether the personalized function is in an enabled state during measurement and whether the estimation result of the state shows that the state during measurement is appropriate for measurement. As a result, it is possible to detect spoofing in which another user different from the intended user carries out measurement using the biological information measuring device 20.

In the example illustrated in FIG. 1, one biological information measuring device 20 is illustrated. The user terminal 30 may be connectable to a plurality of biological information measuring devices 20, and the measurement results acquired by these biological information measuring devices 20 can be individually authenticated. In this embodiment, authentication of a measurement result acquired using a certain biological information measuring device can be performed without using a measurement result acquired using another biological information measuring device.

The authentication system 10 is not limited to a system for computing insurance premiums, and may also be applied to other systems. For example, the authentication system 10 may be applied to a system for returning a portion of a medical cost of a user who has made a lifestyle improvement, a system for epidemiological investigation and research on the relationship between long-term blood pressure changes and the risk of event occurrence or the like, a system for changing dosage depending on the blood pressure of the patient, and the like.

Next, the authentication system 10 will be described in more detail. The following mainly focuses on an example in which the biological information measuring device 20 is a blood pressure monitor.

Configuration Example

Hardware Configuration

Biological Information Measuring Device

Figure 2:
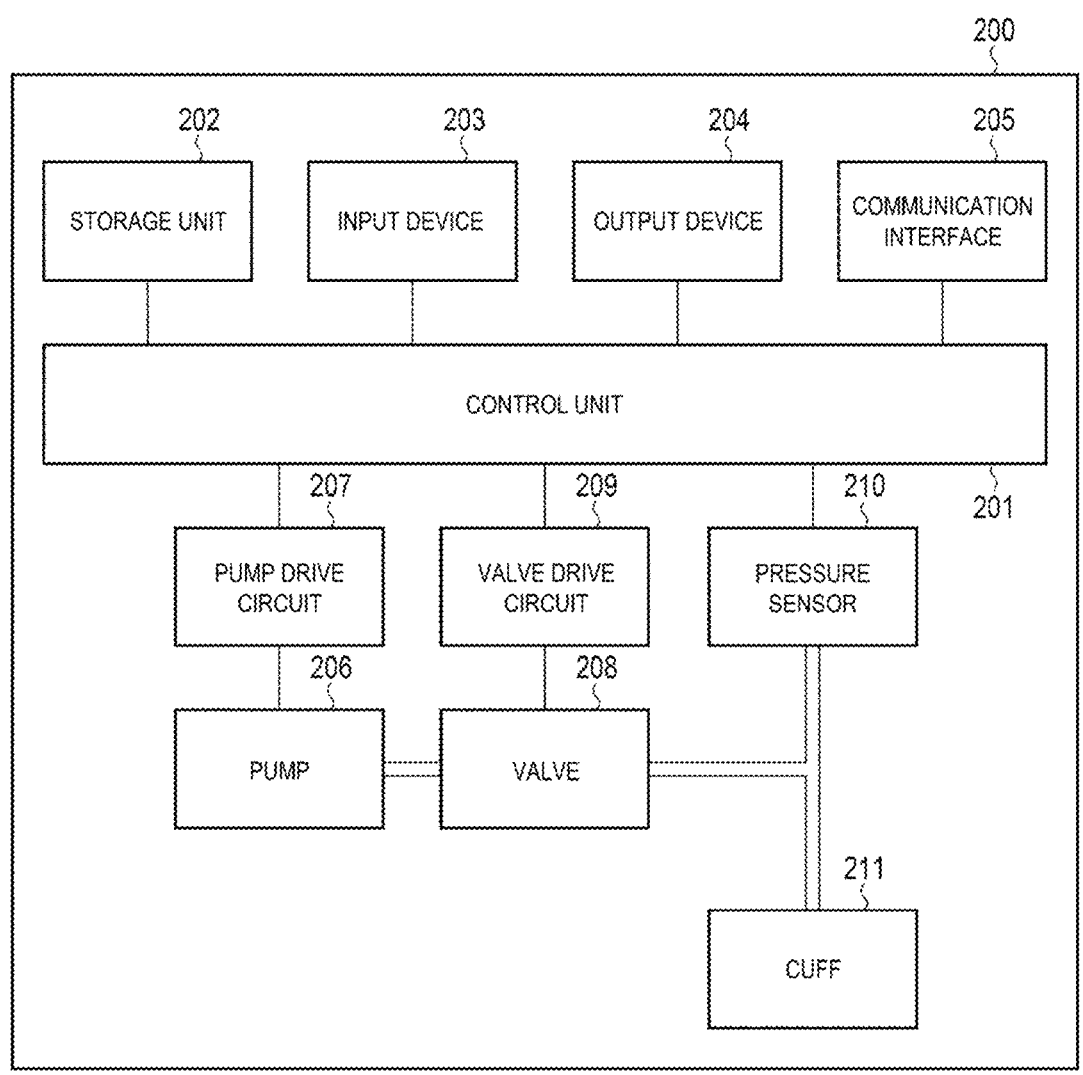
FIG. 2 is a block diagram illustrating an example of a hardware configuration of a biological information measuring device illustrated in FIG. 1.

An example of a hardware configuration of the biological information measuring device 20 according to the present embodiment will be described with reference to FIG. 2. FIG. 2 illustrates an example of the hardware configuration of the biological information measuring device 20. In the example illustrated in FIG. 2, the biological information measuring device 20 is a blood pressure monitor.

In the example in FIG. 2, the biological information measuring device 20 includes a control unit 201, a storage unit 202, an input device 203, an output device 204, a communication interface 205, a pump 206, a pump drive circuit 207, a valve 208, a valve drive circuit 209, a pressure sensor 210, and a cuff 211.

The control unit 201 includes a Central Processing Unit (CPU), a Random Access Memory (RAM), and a Read Only Memory (ROM), and controls each component in accordance with information processing. The storage unit 202 is, for example, an auxiliary storage device such as a hard disk drive (HDD) or a solid state drive (SSD), and stores a blood pressure measurement program executed by the control unit 201, settings data necessary to execute the blood pressure measurement program, measurement data, and the like. A storage medium included in the storage unit 202 is a medium that stores information such as a program by electrical, magnetic, optical, mechanical, or chemical action so that a computer or other device, a machine, or the like can read information such as the recorded program.

The input device 203 is a device that allows a user to enter an instruction for the biological information measuring device 20. For example, the input device 203 includes a push button, such as a button that provides an instruction to start measurement. The output device 204 is a device for performing an output. For example, the output device 204 includes a display device such as a liquid crystal display, and a speaker.

The communication interface 205 is an interface for performing communication. The communication interface 205 includes, but is not limited to, a near-field wireless communication module such as a Bluetooth (trademark) module or a Bluetooth Low Energy (BLE) module. The communication interface 205 may include other types of wireless communication modules, such as a wireless Local Area Network (LAN) module, and may include a wired communication module. Further, the communication between the biological information measuring device 20 and the user terminal 30 is not limited to electromagnetic wave communication, and may be ultrasonic communication, infrared communication, or the like.

The pump 206 is connected to the cuff 211 via a flow path, such as a flexible tube, and supplies air to the cuff 211. The cuff 211 includes an air bag capable of accommodating air. During blood pressure measurement, the cuff 211 is wrapped around the target measurement site (for example, the upper arm) of the subject. The pump drive circuit 207 drives the pump 206 on the basis of a control signal from the control unit 201.

The valve 208 is provided to the flow path. The valve drive circuit 209 drives the valve 208 on the basis of a control signal from the control unit 201. Thus, the valve 208 is switched between an open state and a closed state. When the valve 208 is in the closed state, the flow path is blocked from the atmosphere, and when the valve 208 is in the open state, the flow path communicates with the atmosphere.

The pressure sensor 210 detects pressure in the cuff 211 and generates a pressure signal indicating the detected pressure. As the pressure sensor 210, a piezoresistive pressure sensor can be used, for example. The pressure signal from the pressure sensor 210 is amplified by an amplifier (not illustrated), is converted into a digital signal by an analog to digital conversion circuit (not illustrated), and subsequently provided to the control unit 201.

Note that, with respect to the specific hardware configuration of the biological information measuring device 20, components can be omitted, substituted, and added as appropriate in accordance with the embodiment. For example, the control unit 201 may include a plurality of processors. The biological information measuring device 20 may be a stationary device or a wearable device. For example, in a case where the biological information measuring device 20 is a pedometer or an activity meter, the biological information measuring device 20 is a wearable device.

User Terminal

Figure 3:
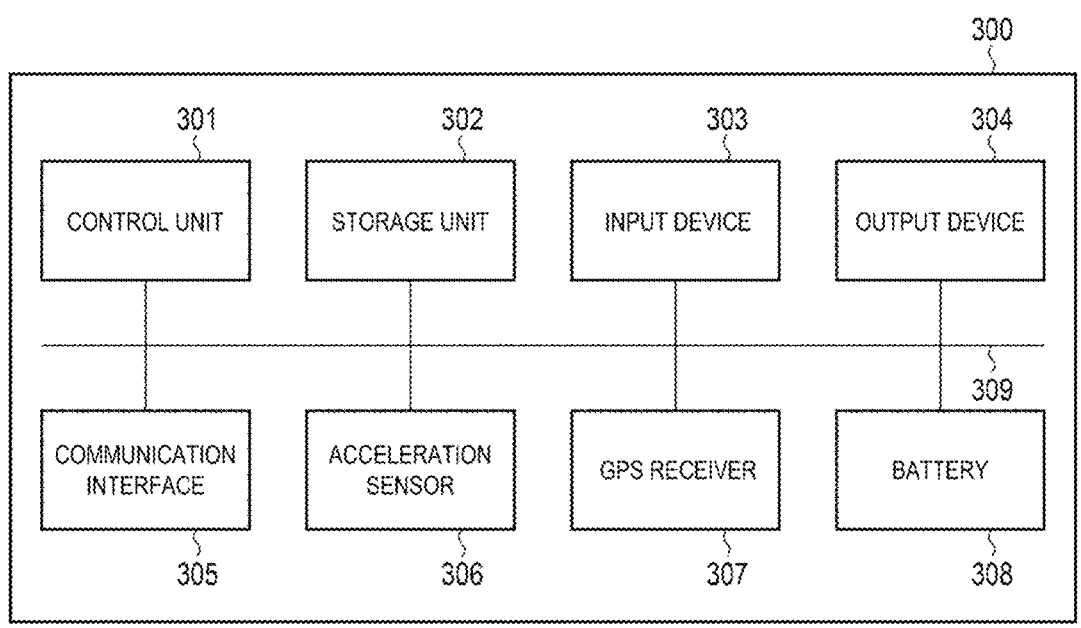
FIG. 3 is a block diagram illustrating an example of a hardware configuration of a user terminal illustrated in FIG. 1.

An example of a hardware configuration of the user terminal 30 according to the present embodiment will be described with reference to FIG. 3. FIG. 3 illustrates an example of the hardware configuration of the user terminal 30. The user terminal 30 is a portable device such as a mobile phone, a smartphone, or a tablet Personal Computer (PC), but is not limited thereto. The user terminal 30 may be a wearable device such as a smart watch.

In the example in FIG. 3, the user terminal 30 includes a control unit 301, a storage unit 302, an input device 303, an output device 304, a communication interface 305, an acceleration sensor 306, a Global Positioning System (GPS) receiver 307, and a battery 308.

The control unit 301 includes a CPU, a RAM, and a ROM, and controls each component in accordance with information processing. The storage unit 302 is, for example, an auxiliary storage device such as an HDD or a SSD, and stores an authentication program executed by the control unit 201, settings data (for example, information indicating a reference behavioral pattern) for executing the authentication program, measurement data received from the biological information measuring device 20, and the like. A storage medium included in the storage unit 302 is a medium that stores information such as a program by electrical, magnetic, optical, mechanical, or chemical action so that a computer or other device, a machine, or the like can read information such as the recorded program.

The input device 303 is a device that allows the user to enter an instruction for the user terminal 30. For example, the input device 303 includes a touch screen, a push button, a microphone, and an imaging device. The output device 204 is a device for performing an output. The output device 204 includes a display device (a display device constituting a touch screen) and a speaker.

The communication interface 305 is an interface for performing communication. The communication interface 305 includes a communication module for communicating with the biological information measuring device 20. For example, the communication interface 305 includes a near-field wireless communication module, such as a Bluetooth module or BLE module.

The communication interface 305 may include other types of wireless communication modules, such as a wireless LAN module, and may include a wired communication module. For example, the communication interface 305 uses a wireless LAN module to communicate with the server 40 via the network NW.

The acceleration sensor 306 detects acceleration of the user terminal 30 and is, for example, a 3-axis acceleration sensor that detects acceleration in a 3-axis direction. The GPS receiver 307 receives GPS signals from a plurality of GPS satellites and outputs the received GPS signals to the control unit 301. The control unit 301 calculates the position of the user terminal 30, that is, the position of the user holding the user terminal 30, on the basis of the GPS signals. The GPS receiver 307 and the control unit 301 form a position sensor for detecting the position of the user terminal 30. Note that the position sensor is not limited to a GPS, and may be based on other satellite navigation such as a Global Navigation Satellite System (GLONASS). The position sensor may also be based on indoor positioning, such as Wi-Fi (trademark) positioning, instead of or in addition to satellite navigation.

The battery 308 can be, for example, a rechargeable battery. The battery 308 supplies power to the control unit 301, the storage unit 302, the input device 303, the output device 304, the communication interface 305, the acceleration sensor 306, and the GPS receiver 307.

Note that, with respect to the specific hardware configuration of the user terminal 30, components can be omitted, substituted, and added as appropriate in accordance with the embodiment. For example, the control unit 301 may include a plurality of processors. The user terminal 30 may further include a gyro sensor that detects an angular velocity of the user terminal 30. A gyro sensor is, for example, a 3-axis gyro sensor that detects an angular velocity about three axes.

Software Configuration

Biological Information Measuring Device

Figure 4:
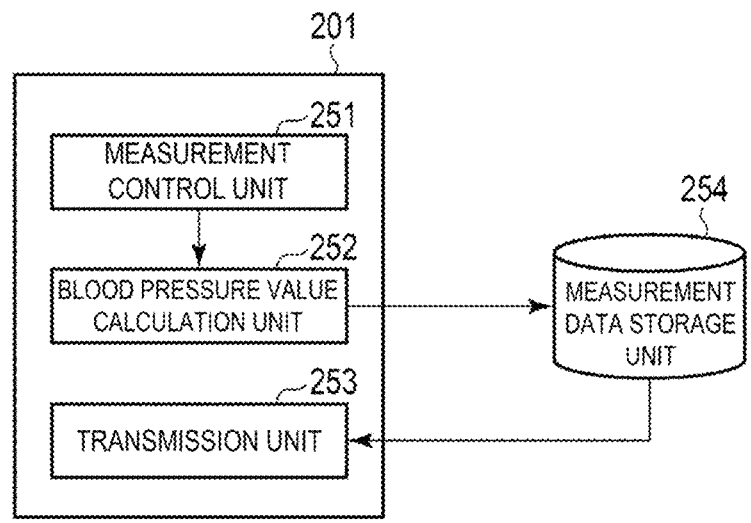
FIG. 4 is a block diagram illustrating an example of a software configuration of the biological information measuring device illustrated in FIG. 1.

An example of a software configuration of the biological information measuring device 20 according to the present embodiment will be described with reference to FIG. 4. FIG. 4 illustrates an example of the software configuration of the biological information measuring device 20. In the example illustrated in FIG. 4, similar to the example described with reference to FIG. 2, the biological information measuring device 20 is a blood pressure monitor.

In the example of FIG. 4, the biological information measuring device 20 includes a measurement control unit 251, a blood pressure value calculation unit 252, a transmission unit 253, and a measurement data storage unit 254. The functions of the measurement control unit 251, the blood pressure value calculation unit 252, and the transmission unit 253 are achieved by the control unit 201 of the biological information measuring device 20 executing a blood pressure measurement program stored in the storage unit 202. When the control unit 201 executes the blood pressure measurement program, the control unit 201 copies the blood pressure measurement program to the RAM. Then, the control unit 201 causes the CPU to interpret and execute the blood pressure measurement program copied to the RAM to control each component. The measurement data storage unit 254 is provided to the storage unit 202.

The measurement control unit 251 controls the blood pressure measurement. Specifically, the measurement control unit 251 controls the operation of the pump 206 and the valve 208. Upon receiving an instruction for starting measurement entered by the subject (for example, intended user) using the input device 203, the measurement control unit 251 causes the valve 208 to close and drives the pump 206. This initiates the supply of air to the cuff 211. The cuff 211 expands, thereby compressing the upper arm of the subject. The measurement control unit 251 monitors the pressure in the cuff 211 indicated by the output signal of the pressure sensor 210. When the pressure in the cuff 211 reaches a predetermined pressure (for example, 300 mmHg), the measurement control unit 251 stops the pump 206 and causes the valve 208 to open. Air is thereby exhausted from the cuff 211.

The blood pressure value calculation unit 252 calculates the blood pressure value by an oscillometric method on the basis of a pressure signal output from the pressure sensor 210 in a pressurization process for supplying air to the cuff 211 or in a depressurization process for exhausting air from the cuff 211. The blood pressure value includes, but is not limited to, systolic blood pressure (SBP) and diastolic blood pressure (DBP). The blood pressure value calculation unit 252 can calculate the pulse rate simultaneously with the blood pressure value. The blood pressure value calculation unit 252 stores the measured value, which is the calculated blood pressure value, in association with the measurement time information in the measurement data storage unit 254. The measurement data storage unit 254 stores measurement data including the measured value and measurement time information associated with the measured value.

The transmission unit 253 reads the measurement data from the measurement data storage unit 254, and transmits the read measurement data to the user terminal 30. The measurement data may be transmitted by unicast communication or by broadcast communication. In a case where the measurement data is transmitted by unicast communication, information pertaining to the intended user including information related to the user terminal 30 is registered in the biological information measuring device 20 in advance. For example, in a case where Bluetooth is employed as the communication method, the intended user performs pairing between the user terminal 30 and the biological information measuring device 20.

The biological information measuring device 20 can be shared by a plurality of users, such as members of a family, for example. In this case, information pertaining to the individual users is registered in the biological information measuring device 20 in advance, and each user selects a registration number corresponding to himself or herself using the input device during measurement. Thus, the transmission unit 253 can designate the user terminal 30 corresponding to the user who carried out measurement, and transmit the measurement data.

In the present embodiment, the measurement data is transmitted using near-field wireless communication. In this case, even in a case where another user different from the intended user selects the registration number corresponding to the intended user and carries out measurement, the user terminal 30 does not receive the measurement data pertaining to the other user when the intended user holding the user terminal 30 is not near the biological information measuring device 20 during the transmission period. For example, the transmission unit 253 transmits measurement data only for a predetermined time (for example, one minute) after measurement. With the measurement data thus transmitted by near-field wireless communication, it is possible to prevent the user terminal 30 from acquiring measurement data pertaining to another user.

Ultrasonic communication may be used as the near-field wireless communication. Ultrasonic communication can be designed to have a short communication distance (for example, approximately 10 to several tens of cm). Thus, this can more effectively prevent the user terminal 30 from acquiring measurement data pertaining to other users.

Note that the biological information measuring device 20 may be connectable to the network NW. In this case, the biological information measuring device 20 can transmit measurement data to the user terminal 30 via the network NW.

User Terminal

Figure 5:
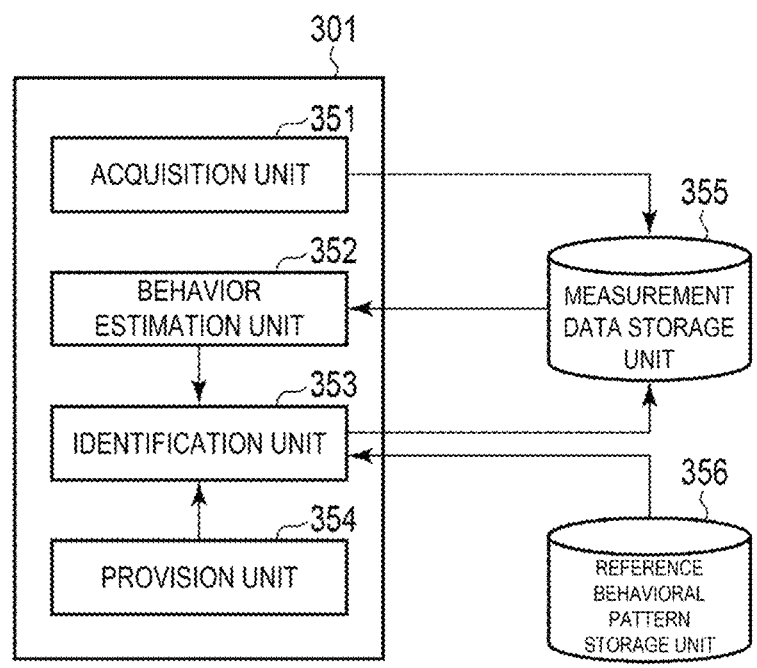
FIG. 5 is a block diagram illustrating an example of a software configuration of the user terminal illustrated in FIG. 1.

An example of a software configuration of the user terminal 30 according to the present embodiment will be described with reference to FIG. 5. FIG. 5 illustrates an example of the software configuration of the user terminal 30.

In the example illustrated in FIG. 5, the user terminal 30 includes an acquisition unit 351, a behavior estimation unit 352, an identification unit 353, a provision unit 354, a measurement data storage unit 355, and a reference behavioral pattern storage unit 356. Functions of the acquisition unit 351, the behavior estimation unit 352, the identification unit 353, and the provision unit 354 are achieved by the control unit 301 of the user terminal 30 executing an authentication program stored in the storage unit 302. When the control unit 301 executes the authentication program, the control unit 301 copies the authentication program to the RAM. Then, the control unit 301 causes the CPU to interpret and execute the authentication program copied to the RAM to control each component. The measurement data storage unit 355 and the reference behavioral pattern storage unit 356 are provided to the storage unit 302.

The provision unit 354 provides personalized functions, for example, a telephone function and an email function. Note that the personalized functions are not limited to being achieved by software executed by the CPU. The personalized functions may be provided by hardware, such as an integrated circuit (IC) chip.

The acquisition unit 351 acquires measurement data from the biological information measuring device 20, and stores the acquired measurement data in the measurement data storage unit 355.

The behavior estimation unit 352 reads the measurement time information included in the measurement data to be processed, and estimates the behavioral pattern of the intended user during a time range specified by the measurement time information. The behavioral pattern includes information indicating whether the intended user was in a static state or a dynamic state. The specified time range includes at least one of a time range before measurement, a time range during measurement, and a time range after measurement. Typically, the specified time range includes at least a time range during measurement. In a case where the biological information measuring device 20 is a blood pressure monitor employing an oscillometric method, the measurement takes several tens of seconds, and the time range during measurement is a period of several tens of seconds in which measurement is performed. Further, the time range before measurement is a period from a time before the measurement start time by a predetermined time (for example, 10 seconds or 1 minute) to the measurement start time, and the time range after measurement is a period from the measurement end time to a time after the measurement end time by a predetermined time (for example, 10 seconds or 1 minute).

The identification unit 353 receives information indicating the behavioral pattern estimated by the behavior estimation unit 352, and reads the information indicating the reference behavioral pattern from the reference behavioral pattern storage unit 356. The reference behavioral pattern is predetermined in accordance with the type of biological information or the type of the biological information measuring device 20. Types of biological information measuring devices include, for example, the type of biological information to be handled and the model (for example, stationary or wearable). FIG. 6 illustrates an example of information indicating a reference behavioral pattern. For example, the reference behavioral pattern associated with the blood pressure monitor is defined as a behavioral pattern in which the user is in a dynamic state before measurement, the user is in a static state during measurement, and the user is in a dynamic state after measurement. The reference behavioral pattern associated with the blood pressure monitor is thus defined because it is common for a user to walk to the location of the blood pressure monitor, remain in place and carry out blood pressure measurement, and take action to leave the location after measurement. In the example illustrated in FIG. 6, the reference behavioral patterns associated with a scale and body composition meter, a thermometer, and an electrocardiograph are the same as the reference behavioral pattern associated with the blood pressure monitor.

The reference behavioral patterns associated with a pedometer and an activity meter are defined as a behavioral pattern in that the user is in a static state before measurement, the user is in a dynamic state during measurement, and the user is in a static state after measurement. The pedometer and the activity meter are constantly carrying out measurement. In a case where the biological information measuring device 20 is a pedometer, a period during which the step count is increasing corresponds to a time range during measurement, and a period during which the step count does not change corresponds to a time range before or after measurement. In a case where the biological information measuring device 20 is an activity meter, a period during which activity is detected corresponds to a time range during measurement, and a period during which no activity is detected corresponds to a time range before or after measurement.

The identification unit 353 determines whether the behavioral pattern estimated by the behavior estimation unit 352 matches the reference behavioral pattern, and determines whether the personalized function is in an enabled state during the measurement time range. In a case where the identification unit 353 determines that the estimated behavioral pattern matches the reference behavioral pattern and that the personalized function was in an enabled state during the measurement time range, the identification unit 353 identifies that the measured value included in the measurement data to be processed pertains to the intended user, and applies attribute information indicating that the measured value pertains to the intended user to the measurement data to be processed. In a case where the identification unit 353 determines that the estimated behavioral pattern does not match the reference behavioral pattern or that the personalized function was not in an enabled state during the measurement time range, the identification unit 353 identifies that the measured value included in the measurement data to be processed does not pertain to the intended user, and applies attribute information indicating that the measured value does not pertain to the intended user to the measurement data to be processed.

For blood pressure measurement, it is desirable for the intended user to be in a resting state for a certain period of time (for example, several minutes) before measurement. In a case where the biological information measuring device 20 is a blood pressure monitor, the behavior estimation unit 352 may further estimate the behavior of the user at a time before measurement (e.g., a time from 5 minutes before measurement to 1 minute before measurement). This makes it possible to acquire information indicating whether resting time was ensured before measurement as additional information.

Note that in the present embodiment, an example is described in which both the functions of the biological information measuring device 20 and the user terminal 30 are achieved by a general-purpose CPU. However, a portion or all of the functions may be achieved by one or a plurality of dedicated processors. Further, components of the biological information measuring device 20 and the user terminal 30 may be omitted, substituted, and added as appropriate in accordance with the embodiment.

Operational Example

Figure 7:
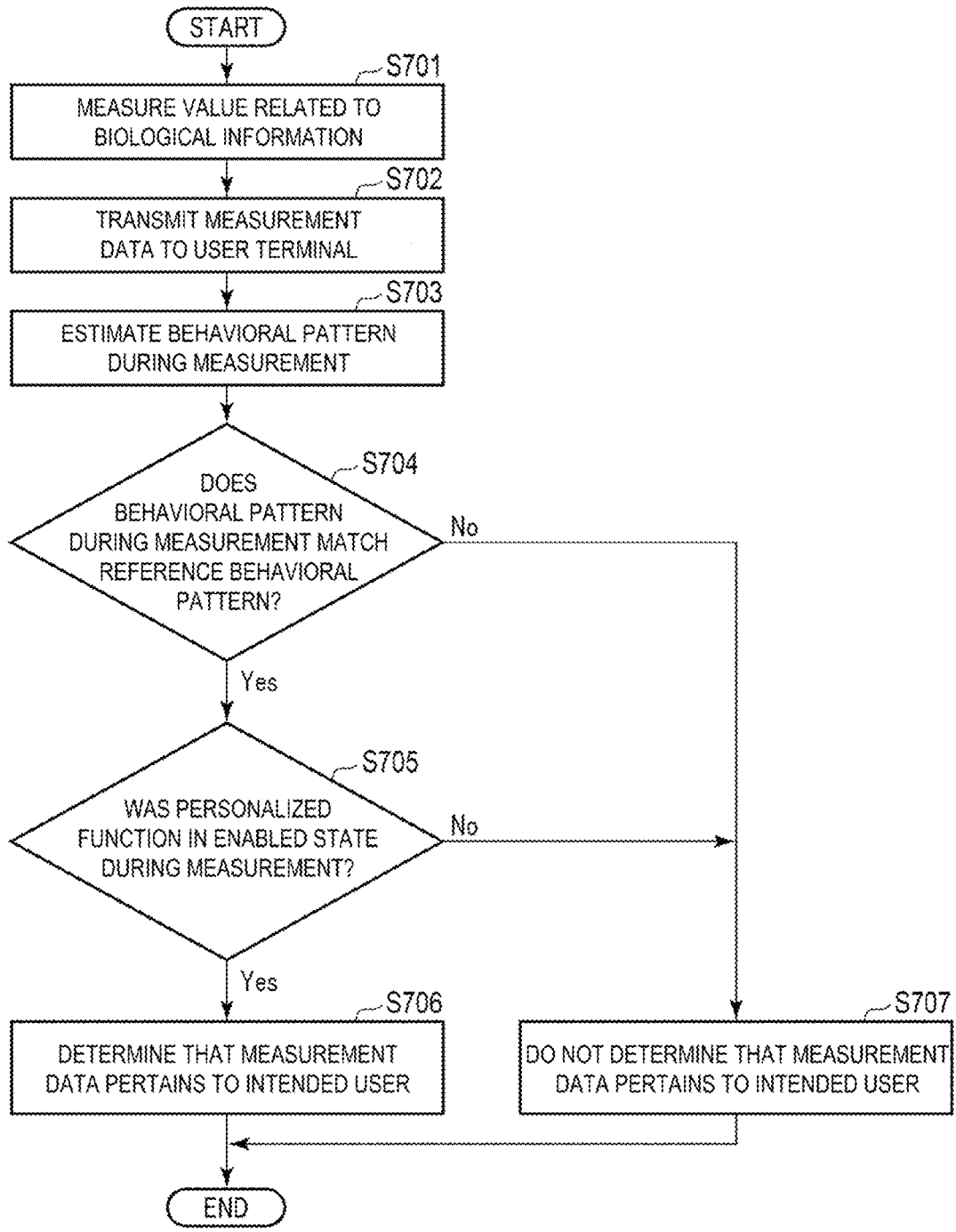
FIG. 7 is a flowchart illustrating an example of a processing procedure of the authentication system illustrated in FIG. 1.

With reference to FIG. 7, an operation example of the authentication system 10 will be described. The processing procedure described below is merely an example, and each step may be changed to the extent possible. Further, in the processing procedure described below, steps can be omitted, substituted, and added in accordance with the embodiment.

In step S701 of FIG. 7, the biological information measuring device 20 measures a value related to the biological information, and generates measurement data including the measured value and the measurement time information. For example, the control unit 201 of the biological information measuring device 20 operates as the measurement control unit 251 to control the valve drive circuit 209 and the pump drive circuit 207, causing the valve 208 to be in a closed state and the pump 206 to supply air to the cuff 211. The control unit 201 operates as the blood pressure value calculation unit 252, and calculates a blood pressure value on the basis of the pressure signal output from the pressure sensor 210. When the blood pressure value is calculated, the control unit 201 operates as the measurement control unit 251, and controls the pump drive circuit 207 and the valve drive circuit 209, causing the pump 206 to stop supplying air and the valve 208 to be in an open state. The measurement time information may be, for example, a time at which the blood pressure value is calculated as the measured value, or may be a time at which a user presses a measurement start button.

In step S702, the biological information measuring device 20 transmits the measurement data to the user terminal 30. For example, the control unit 201 operates as the transmission unit 253, and wirelessly transmits measurement data to the user terminal 30 via the communication interface 205.

The user terminal 30 receives measurement data from the biological information measuring device 20. For example, the control unit 301 of the user terminal 30 operates as the acquisition unit 351, receives measurement data from the biological information measuring device 20 via the communication interface 305, and stores the received measurement data in the measurement data storage unit 355.

In the present embodiment, the biological information measuring device 20 directly transmits measurement data to the user terminal 30 by near-field wireless communication. Thus, in a case where the user terminal 30 is not near the biological information measuring device 20, the measurement data is not received by the user terminal 30. The user terminal 30 not being near the biological information measuring device 20 corresponds to the intended user not being near the biological information measuring device 20, that is, the intended user not having carried out measurement using the biological information measuring device 20. In a case where the measurement data is transmitted directly from the biological information measuring device 20 to the user terminal 30 by near-field wireless communication, the user terminal 30 can be prevented from receiving measurement data pertaining to others. As a result, an authentication accuracy can be improved.

In step S703, the user terminal 30 estimates the behavioral pattern of the user when the measured value included in the measurement data was acquired. For example, the control unit 301 operates as the behavior estimation unit 352, and specifies a measurement time range on the basis of the measurement time information included in the measurement data. Subsequently, the control unit 301 estimates the behavioral pattern of the user in the specified time range. For example, the measurement time range includes a time range before measurement, a time range during measurement, and a time range after measurement, and the control unit 301 determines whether the user was in a static state or in a dynamic state in each time range. For example, the control unit 301, upon detecting movement (for example, walking or running) during each of the time ranges, determines that the user is in a dynamic state during the time range, and, upon not detecting movement during each of the time ranges, determines that the user was in a static state during the time range. Whether the user has carried out a movement associated with a change in location can be detected on the basis of an acceleration signal output from the acceleration sensor 306 and position information output from a position sensor.

In step S704, the user terminal 30 determines whether the behavioral pattern thus estimated (estimated behavioral pattern) matches the reference behavioral pattern. In a case where the estimated behavioral pattern matches the reference behavioral pattern, the flow proceeds to step S705, and in a case where the estimated behavioral pattern does not match the reference behavioral pattern, the flow proceeds to step S707.

For example, the control unit 301 operates as the identification unit 353, reads the reference behavioral pattern corresponding to the target type of biological information from the reference behavioral pattern storage unit 356, and determines whether the estimated behavioral pattern matches the read reference behavioral pattern. In a case where the biological information measuring device 20 is a blood pressure monitor, a reference behavioral pattern associated with blood pressure monitor is read. As illustrated in FIG. 6, the reference behavioral pattern associated with blood pressure monitor is a pattern in that the user is in a dynamic state during the time range before measurement, the user is in a static state during the time range during measurement, and the user is in a dynamic state during time range after measurement. In this case, the control unit 301 determines that the estimated behavioral pattern matches the reference behavioral pattern in a case where the estimated behavioral pattern is in a dynamic state during the time range before measurement, a static state during the time range during measurement, and a dynamic state during the time range after measurement, and determines that the estimated behavioral pattern does not match the reference behavioral pattern in all other cases.

In step S705, the user terminal 30 determines whether the personalized function was in an enabled state throughout the measurement time range. In a case where the personalized function was in an enabled state throughout the measurement time range, the flow proceeds to step S706. Otherwise, the flow proceeds to step S707.

For example, the control unit 301 operates as the identification unit 353, and determines whether the personalized function was in an enabled state during the measurement time range. In a case where the control unit 301 determines that the personalized function was in an enabled state during the measurement time range, the control unit 301 determines that the intended user have been holding the user terminal 30, and in a case where the control unit 301 determines that the personalized function is not in an enabled state during the measurement time range, the control unit 301 determines that another user may have been holding the user terminal 30.

In step S706, the user terminal 30 determines that the measured value included in the measurement data pertains to the intended user. For example, the control unit 301 operates as the identification unit 353, and identifies that the measured value included in the measurement data pertains to the intended user. In this case, for example, attribute information indicating that the measured value pertains to the intended user is added to the measurement data.

In step S707, the user terminal 30 does not determine that the measured value included in the measurement data pertains to the intended user. For example, the control unit 301 operates as the identification unit 353, and identifies that the measured value included in the measurement data does not pertain to the intended user. In this case, for example, attribute information indicating that the measured value does not pertain to the intended user is added to the measurement data. Note that the control unit 301 may discard measurement data to be processed.

In this way, the measurement data acquired by the biological information measuring device 20 is accumulated in the user terminal 30. The measurement data accumulated in the user terminal 30 is transmitted appropriately to the server 40 over the network NW.

Effect

In the present embodiment, a personalized function is provided to the user terminal 30. When the personalized function is in an enabled state, it is ensured that the specific user is holding the user terminal 30. Thus, in a case where the personalized function is in an enabled state during measurement, the estimation result of the state during measurement is regarded as a result pertaining to the intended user. Further, in a case where the intended user himself or herself carries out measurement using the biological information measuring device 20, the behavioral pattern of the intended user should match the reference behavioral pattern. Thus, on the basis of whether the personalized function is in an enabled state during measurement and whether the estimated behavioral pattern matches the reference behavioral pattern, the measured value included in the measurement data can be authenticated. As a result, spoofing in which another user different from the intended user carries out measurement using the biological information measuring device 20 can be detected.

By estimating the behavior of the user during the time range during measurement as well as the time range before measurement and/or the time range after measurement, it is possible to improve the authentication accuracy to a greater extent than when the behavior of the user is estimated only during the time range during measurement.

Modified Example

The present invention is not limited to the embodiments described above. For example, in the embodiments described above, the behavioral pattern of the user is estimated as the state of the user. In contrast, in another embodiment, whether the user is in a predetermined environment may be estimated as the state of the user. In this case, instead of the behavior estimation unit 34, the user terminal 30 includes an environment estimation unit that estimates whether the intended user is in a predetermined environment. The environment estimation unit corresponds to the "estimation unit" of the present invention. The sensor unit 33 is configured to detect whether the intended user is in a predetermined environment and includes, for example, an optical sensor that detects a surrounding brightness. The environment estimation unit estimates, on the basis of the surrounding brightness detected by the optical sensor, whether the intended user is in a bright location or a dark location during the time range for measurement. The estimation can be based on, for example, a comparison of the brightness detected by the optical sensor and a threshold. The identification unit 35 identifies that the measured value pertains to the intended user in a case where the environment estimation unit estimates that the intended user is in a bright location, and identifies that the measured value does not pertain to the intended user in a case where the environment estimation unit estimates that the intended user is in a dark location. This identification method is based on the general circumstance that biological information such as blood pressure is not measured in a dark location.

Further, a portion or all of the processing related to authentication may be executed on a device (for example, the server 40) different from the user terminal 30. For example, the server 40 may include the behavior estimation unit 34 and the identification unit 35. In this case, the user terminal 30 transmits information acquired by the sensor unit 33, information indicating the state of the personalized function, and measurement data acquired by the biological information measuring device 20 to the server 40 over the network NW. Note that the biological information measuring device 20 may transmit measurement data to the server 40 over the network NW without using the user terminal 30.

The present invention is not limited to the embodiments described above, and can be embodied by modifying the components in an implementation stage without departing from the gist thereof. Further, various inventions can be formed by appropriate combinations of the plurality of components disclosed in the embodiments described above. For example, from among all components illustrated in the embodiments, several components may be deleted. Furthermore, components of different embodiments may be combined as appropriate.

REFERENCE SIGNS LIST

1 Information processing system
10 Authentication system
20 Biological information measuring device
21 Measurement unit
22 Communication unit
201 Control unit
202 Storage unit
203 Input device
204 Output device
205 Communication interface
206 Pump
207 Pump drive circuit
208 Valve
209 Valve drive circuit
210 Pressure sensor
211 Cuff
251 Measurement control unit
252 Blood pressure value calculation unit
253 Transmission unit
254 Measurement data storage unit
30 User terminal
31 Communication unit
32 Personalized function provision unit
33 Sensor unit
34 Behavior estimation unit
35 Identification unit
301 Control unit
302 Storage unit
303 Input device
304 Output device
305 Communication interface
306 Acceleration sensor
307 GPS receiver
308 Battery
351 Acquisition unit
352 Behavior estimation unit
353 Identification unit
354 Provision unit
355 Measurement data storage unit
356 Reference behavioral pattern storage unit
40 Server

The invention claimed is:

1. An authentication device comprising:
a communication interface configured to receive measurement data including a measured value and measurement time information associated with the measured value from a biological information measuring device configured to measure a value related to blood pressure, the measurement time information indicating a time at which measurement of the blood pressure is carried out;
a sensor unit including at least one sensor; and
a controller configured to:
provide a function to be used by one specific user;
estimate, on the basis of information acquired by the sensor unit, a state of the one specific user during a time range specified by the measurement time information, the state of the one specific user including a behavioral pattern comprising information indicating whether the one specific user is in a static state or a dynamic state during the measurement of the blood pressure;
identify that the measured value pertains to the one specific user in a case where the function is in an enabled state during the time range and a behavioral pattern estimated by the controller matches a reference behavioral pattern associated with the blood pressure; and
identify that the measured value does not pertain to the one specific user in a case where the function is not in an enabled state during the time range or the behavioral pattern estimated by the controller does not match the reference behavioral pattern associated with the blood pressure, the reference behavioral pattern associated with the blood pressure being defined as a behavioral pattern in which a user is in a static state during the measurement of the blood pressure.

2. The authentication device according to claim 1, wherein
the communication interface is configured to receive the measurement data by near-field wireless communication with the biological information measuring device.

3. A non-transitory storage medium storing a program for causing a computer to function as the controller included in the authentication device according to claim 2.

4. The authentication device according to claim 2, wherein the near-field wireless communication is ultrasonic communication.

5. A non-transitory storage medium storing a program for causing a computer to function as the controller included in the authentication device according to claim 4.

6. A non-transitory storage medium storing a program for causing a computer to function as the controller included in the authentication device according to claim 1.

7. An authentication system comprising:
a biological information measuring device; and
an authentication device capable of communicating with the biological information measuring device, wherein
the biological information measuring device includes
a measurement unit configured to measure a value related to blood pressure, an electrocardiogram, and
a first communication interface configured to transmit measurement data including a measured value acquired by the measurement unit, and measurement time information associated with the measured value, measurement time information indicating a time at which measurement of the blood pressure is carried out, and
the authentication device includes
a second communication interface configured to receive the measurement data from the biological information measuring device,
a sensor unit including at least one sensor, and
a controller configured to
provide a function to be used by one specific user,
estimate, on the basis of information acquired by the sensor unit, a state of the one specific user during a time range specified by the measurement time information, the state of the one specific user including a behavioral pattern comprising information indicating whether the one specific user is in a static state or a dynamic state during the measurement of the blood pressure, identify that the measured value pertains to the one specific user in a case where the function is in an enabled state during the time range and a behavioral pattern estimated by the controller matches a reference behavioral pattern associated with the blood pressure; and identify that the measured value does not pertain to the one specific user in a case where the function is not in an enabled state during the time range or the behavioral pattern estimated by the controller does not match the reference behavioral pattern associated with the blood pressure, the reference behavioral pattern associated with the blood pressure being defined as a behavioral pattern in which a user is in a static state during the measurement of the blood pressure.

8. An authentication method executed by an authentication device including a sensor unit including at least one sensor, the authentication method comprising the steps of:

acquiring measurement data including a measured value and measurement time information associated with the measured value from a biological information measuring device configured to measure a value related to blood pressure, the measurement time information indicating a time at which measurement of the blood pressure is carried out;

providing a function to be used by one specific user;

estimating, on the basis of information acquired by the sensor unit, a state of the one specific user during a time range specified by the measurement time information, the state of the one specific user including a behavioral pattern comprising information indicating whether the one specific user is in a static state or a dynamic state during the measurement of the blood pressure;

identifying that the measured value pertains to the one specific user in a case where the function is in an enabled state during the time range and behavioral pattern estimated by the controller matches a reference behavioral pattern associated with the blood pressure; and identifying that the measured value does not pertain to the one specific user in a case where the function is not in an enabled state during the time range or the behavioral pattern estimated by the controller does not match the reference behavioral pattern associated with the blood pressure, the reference behavioral pattern associated with the blood pressure being defined as a behavioral pattern in which a user is in a static state during the measurement of the blood pressure.

* * * * *